United States Patent [19]

Meyer-Arendt

[11] 4,236,821

[45] Dec. 2, 1980

[54] METHOD AND APPARATUS FOR TESTING OPTICAL RETRODIRECTIVE PRISMS

[75] Inventor: Jurgen R. Meyer-Arendt, Forest Grove, Oreg.

[73] Assignee: McHenry Systems, Inc., Donald, Oreg.

[21] Appl. No.: 65,531

[22] Filed: Aug. 10, 1979

[51] Int. Cl.³ .................... G01B 9/00; G01N 21/01
[52] U.S. Cl. .................... 356/124; 350/102; 350/173; 350/276 R; 356/448
[58] Field of Search .................. 356/124, 445, 448; 350/101, 102, 103, 173, 285, 276 R

[56] References Cited

U.S. PATENT DOCUMENTS

| | | | |
|---|---|---|---|
| 2,106,752 | 2/1938 | Land | 354/117 |
| 2,747,460 | 5/1956 | Calvi | 353/33 |
| 3,578,869 | 5/1971 | Irland et al. | 356/239 |
| 3,836,232 | 9/1974 | Hall, Jr. | 350/174 |
| 3,844,638 | 10/1974 | Lingenfelder et al. | 350/171 |
| 3,977,789 | 8/1976 | Hunter et al. | 356/124 X |
| 4,171,910 | 10/1979 | Derderian et al. | 356/124 |

FOREIGN PATENT DOCUMENTS

1321133  2/1963  France ..................... 356/124

*Primary Examiner*—John K. Corbin
*Assistant Examiner*—Bruce Y. Arnold
*Attorney, Agent, or Firm*—Eugene D. Farley

[57] ABSTRACT

Retrodirective optical prisms are tested for light reflection and efficiency by generating two substantially coaxial beams of light, a signal beam and a reference beam. The beams are passed through an optical beam splitter arranged at a predetermined angle to the axis of the beams, thereby separating them. The separated signal beam is passed into the prism to be tested, reflected back along its initial path, and back through the beam splitter. The intensity of the reflected beam is measured and compared with the intensity of the reference beam. It thus gives an indication of the light reflective efficiency of the prism.

18 Claims, 11 Drawing Figures

METHOD AND APPARATUS FOR TESTING OPTICAL RETRODIRECTIVE PRISMS

BACKGROUND AND GENERAL STATEMENT OF THE INVENTION

This invention pertains to method and apparatus for testing the light reflective efficiency of retrodirective optical prisms.

The invention pertains particularly to method and apparatus for the testing and quality control of retrodirective or cube corner reflectors, referred to in the art, and herein, as "prisms". Such reflectors are necessary components of land survey apparatus and distance measuring apparatus, and are used as well in other geodetic applications. Their principal characteristic is that they return a beam of light in its initial path.

However, the degree to which this is accomplished clearly depends upon the precision and accuracy with which the prisms are manufactured. Manufacturers and distributors of such prisms therefore use various means to make sure that the prisms they make, receive, or sell, meet certain criteria. In short, they employ various means for quality control.

Foremost among these is testing by interferometry. Interferometry is widely considered to be a very precise and most accurate measurement tool. In particular, the analysis of interference effects (interference fringes) can be used to determine the correct shape of the prisms. It also can be used to indicate deviations, if any, from true right angles, inhomogeneities within the glass, and other dimensional and optical defects. Some manufacturers even supply interferograms with the prisms they sell, and a number of publications are concerned with the generation and interpretation of fringes that are produced by optical interference.

A general overview, and a more detailed discussion of interferometry and photometry, is found in Jurgen R. Meyer-Arendt, "Introduction to Classical and Modern Optics," Prentice-Hall, Inc., Englewood Cliffs, New Jersey 1972, 4th printing 1978. For a detailed mathematical analysis of cube corner retrodirective reflectors see Edson R. Peck, "Theory of the Corner-Cube Interferometer", Journal of the Optical Society of America, Volume 38, pages 1015–1024 (1948). Interferometry as a rapid method for testing retrodirective prisms has been described by David A. Thomas and J. C. Wyant, "Determination of the Dihedral Angle Errors of a Corner Cube from its Twyman-Green Interferogram", Journal of the Optical Society of America, Volume 67, pages 467–472 (1977).

Practical experience has taught, however, that in actual use in the field some retrodirective prisms perform very well while others do not, and that these differences in performance are not necessarily related to the interference patterns of the prisms. Some prisms have deficiencies that cannot be detected by interferometry. Examples of such defects are dust on the prism surface, weathering and other causes of dullness of the glass, frustrated internal reflection (in non-metallized prisms), defective reflective coatings (in coated prisms), and absorption within the glass. Most importantly, it is the strength of the return signal that determines the practical use value of retrodirective prisms, not the results of interferometry as such.

Accordingly, it is the general object of the present invention to provide a practical, accurate, easily carried out method for the testing and evaluation of retrodirective optical prisms by measuring the intensity of a light signal reflected therefrom and by comparing that intensity with the intensity of a reference beam.

It is another principal object of the present invention to provide simple, accurate, and easily operated apparatus for carrying out the test method.

The foregoing and other objects of this invention are accomplished by the practice of a method which, broadly considered comprises generating two substantially coaxial beams of light, a signal beam and a reference beam. The beams are passed through an optical beam splitter which is adjusted at a predetermined angle to the axis of the beams, i.e. at an angle of $\pm 10°$ preferably $\pm 5°$. This separates the beams.

The separated signal beam then is passed into the prism to be tested. It is reflected out of the prism parallel to its initial path, and back through the beam splitter. The intensity of the reflected beam is measured and preferably compared with the intensity of the separated reference beam. This gives a measure of the amount of light reflected by the prism and accordingly of its efficiency.

The separated reference beam is either absorbed, or its intensity measured and used as a comparison standard.

Broadly considered, the apparatus of the present invention comprises means for accomplishing the functions above indicated.

DESCRIPTION OF PREFERRED EMBODIMENTS OF THE INVENTION

Figure 1:
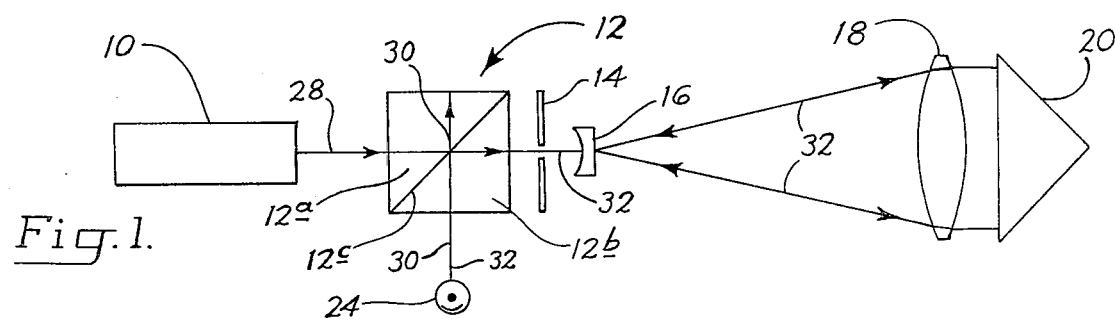
FIG. 1 is a schematic view of the presently described apparatus for testing optical retrodirective prisms, with its beam splitter component in aligned position, using a laser light source.
Figure 2:
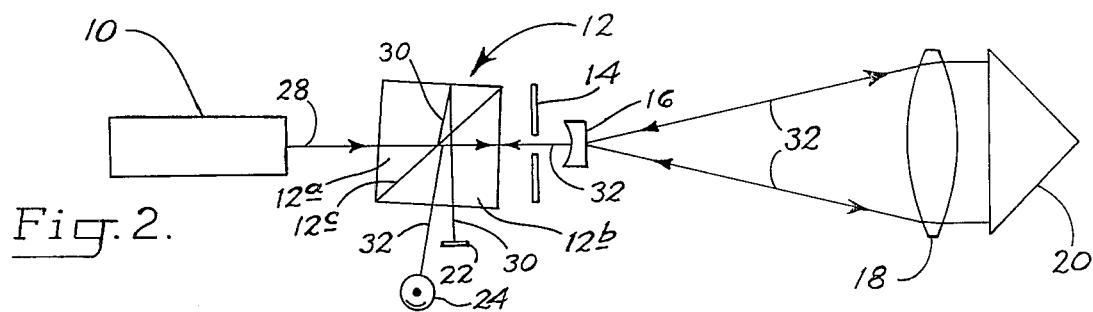
FIG. 2 is a view similar to FIG. 1, with the beam splitter component in an adjusted angular position.
Figure 3:
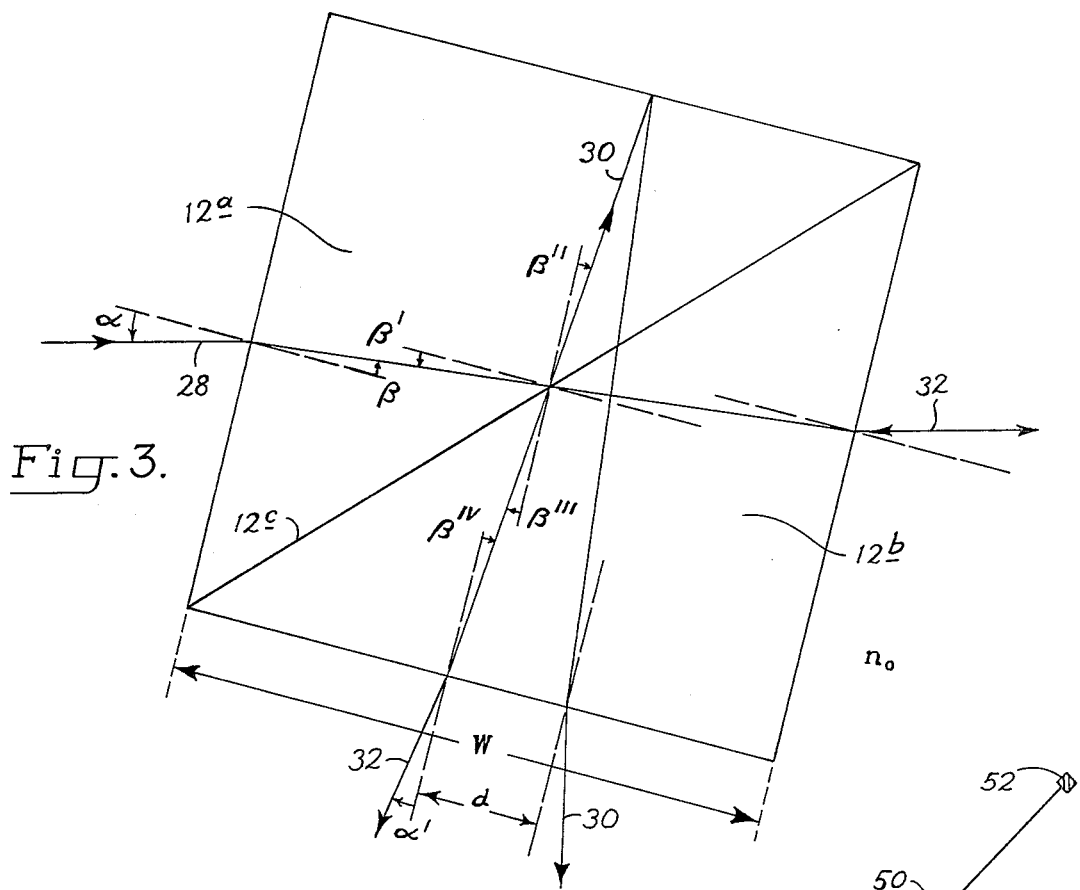
FIG. 3 is an enlarged view of the beam splitter component of the invention in its glass cube embodiment.

Referring to FIGS. 1-3:

The apparatus of the present invention illustrated in these figures comprises light generating means 10, optical beam splitter means 12, pinhole means 14, a diverging or minus lens 16, a positive lens 18, the prism to be tested 20, a light stop 22, and light intensity measuring means 24.

The light generating means 10 employed preferably comprises a conventional laser unit.

The light from this unit may be considered to comprise two beams, a signal beam and a background or reference beam. For the purposes of the invention, it is necessary to separate the former from the latter.

The separation is achieved by passing the beams through optical beam splitter 12.

As is well known, such a beam splitter may comprise a glass cube cut diagonally into two identical halves, 12a and 12b, of triangular cross section. These are cemented together with clear optical cement. This creates the reflective boundary 12c.

The composite light beam 28 leaving generating unit 10 passes through beam splitter 12 and impinges upon boundary 12c, which is set at an angle of 45° to the axis of the light beam. As a result, the reference signal constituted by beam 30 is reflected upwardly and is reflected by the upper surface of the beam splitter so that it travels downwardly along its own path.

Figure 5:
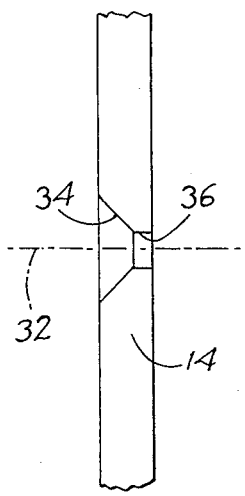
FIG. 5 is a schematic view in elevation of a pinhole component of the apparatus of the invention.

The signal beam 32, however, passes next through pinhole 14. This element of the apparatus is shown in greater detail in FIG. 5.

It comprises a metallic sheet, such as a brass or aluminum sheet, drilled part way through with a conventional drill. This forms the beveled portion 34 of the pinhole aperture.

The sheet then is completely penetrated by means of a hair drill to form the restricted pinhole aperture 36. The restricted or pinhole aperture is faced away from the beam splitter, toward the prism to be tested, for a reason which will appear hereinafter. This construction provides the desired strength while still furnishing a pinhole of very small internal diameter, e.g. a diameter of from a fraction of a millimeter to a few millimeters, preferably about 1.2 millimeters.

The signal beam 32 then is passed through diverging or minus lens 16. The purpose of this lens is to widen the beam so as to fill the aperture of downstream lens 18.

Figure 6:
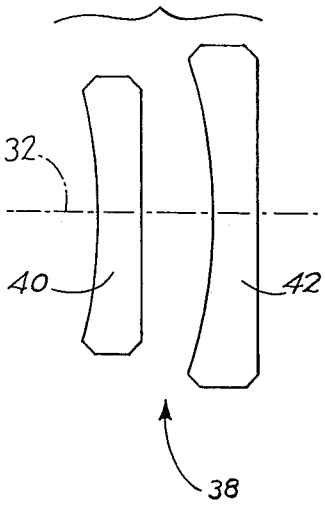
FIG. 6 is a schematic view of a diverging lens component of the apparatus of the invention.

Although lens 16 may be a simple concavo-planar lens, as shown in FIG. 1, it preferably comprises a more complex lens such as the air-spaced doublet 38 illustrated in FIG. 6. While a great variety of such lens systems might be used, I have found satisfactory a combination of a first concavo-plane lens 40 of 10 mm. diameter and minus 20 mm. focal length, and a second concavo-plane lens 42, of 11.5 mm. diameter and minus 27.3 mm. focal length.

Figure 7:
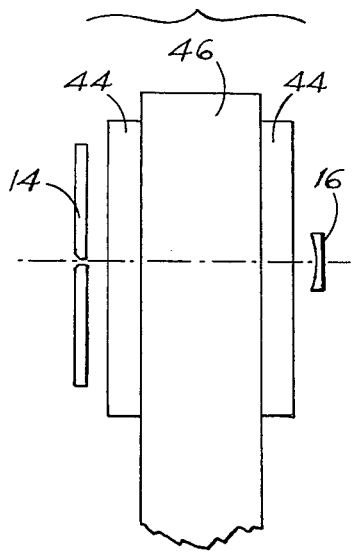
FIG. 7 is a fragmentary schematic view of a mounting for the pinhole and diverging lens components of the apparatus of the invention.

For the successful practice of the invention, pinhole 14 and lens 16 preferably are mounted on x-y cross-motion stages 44. These are mounted back to back on opposite sides of a carrier 46 which in turn rests on the optical bench, FIG. 7.

After leaving lens 16, the divergent signal beam 32 enters a lens 18, the function of which is to cause the divergent light entering it to become parallel again.

Lens 18 is a positive lens of large diameter. This diameter preferably is larger than the diameter of the prism to be tested. Its focal length is governed by the distance from lens 16 to lens 18.

Lens 18 in an actual embodiment of the invention has a diameter of 95 mm. and a focal length of 600 mm.

The parallel light leaving lens 18 enters test prism 20, mounted in a suitable holder, not illustrated. The beam 32 reflected by the prism is reflected back parallel to its initial path. It passes again, but now in reverse order, through lens 18, lens 16, and pinhole 14. Light such as that deviated by imperfections in the reflecting surfaces of the prism, which does not return exactly in its initial path, will be blocked by the sharp edge of the pinhole.

In other words, the pinhole serves to discriminate between, and separate, correctly returned light on the one hand, and deviated light on the other hand, the deviation being caused by imperfections or defects in prism 20.

After passing through pinhole 14 the correctly returned light will fall on boundary 12c of beam splitter 12. By this boundary it will be deflected downwardly out of the beam splitter and passed into photodetector 24.

The latter component of the apparatus may be any unit which is sensitive to light, for example, a photocell which converts light energy to electrical energy. The intensity of the light will determine the strength of the electric current generated and accordingly will give a direct measure of the reflecting efficiency of test prism 20. The current strength, and hence the prism efficiency, may be read directly on an ammeter associated with the photocell.

The response of the photocell accordingly is an indication of how much light has been returned by prism 20. A higher return, in short, means a higher quality prism.

Thus the measurement of light intensity, or photometry, can be applied to the testing and evaluation of retrodirective prisms. In the practical use of this method, however, it is found that any passage of light through the beam splitter 12, and more generally, any return of light in its own path, causes a certain percentage of the light to reach photodetector 24 directly without being reflected by the prism.

Such spurious light has its origin in the reference signal 30 discussed hereinabove. Generated by laser generator 10, the reference signal is reflected from the angled boundary 12c of the beam splitter upwardly against the internal surface of the beam splitter. It then is reflected downwardly in its own path, merges with the retrodirected signal beam 32 reflected by prism 20 and with it enters and energizes photodetector 24.

Clearly such light is highly undesirable because it superimposes on the reflected signal beam and thus impedes the taking of accurate measurements. In the past, extensive analyses, including statistical procedures, were devised to separate the noise from the signal beam and to generally improve the signal-to-noise ratio. The present invention provides a much simpler and more accurate solution to this problem.

In particular, I now have found that the signal-to-noise ratio is greatly increased and the performance of the hereindescribed prism testing apparatus very significantly improved, if beam splitter 12 is purposely misaligned, i.e. turned or rotated through a small angle.

Ordinarily, as shown in FIG. 1, beam splitter 12 is set so that the light is incident on its front surface at right angles.

However, if the beam splitter is rotated so that its front face is not exactly at right angles to the incoming light, this light will fall on boundary 12c at an angle other than 45°. Consequently the light will impinge on the top face of the beam splitter also at an angle other than perpendicular and emerge from the opposite side face of the cube as beam 30.

The signal carrying beam 32, therefore, has been separated in space from the reference beam 30. All that is needed, then, is to insert an apparatus unit in the path of the noise carrying beam to accommodate the same.

Such a unit may comprise unit 22 (FIG. 2) which is either an optical stop or a photodetector. If an optical stop, 22 comprises a solid base having a black, lightabsorbent surface and serves the function of blocking beam 30 from the photodetector 24 while permitting the signal-carrying beam 32 to enter the photodetector 10.

If, in the alternative, 22 is a photodetector, one can then use beam 30 as a comparison beam or internal reference.

Thus both the signal beam and the reference or comparison beam can be directed into separate photodetectors and the strengths of the two signals be compared with each other. This gives a measure of prism efficiency which is independent of such variables as fluctuating voltages in light generating unit 10.

Figure 9:
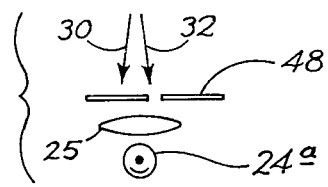
FIG. 9 is a schematic view illustrating alternate means for measuring prism reflectance.

Still another mode of applying this principle is illustrated in FIG. 9.

Signal beam 32 and reference beam 30 both may be directed into single photodetector 24a with lens 25. A shutter 48 may be interposed between the beam splitter and the photodetector. It is arranged in such a manner that upon adjustment of the shutter one or the other of the two beams may be transmitted to the photodetector. In this way two comparative readings may be obtained.

In alternative forms of the invention, a simple glass plate, or a pellicle may be substituted for the glass cube beam splitter 12.

Figure 4:
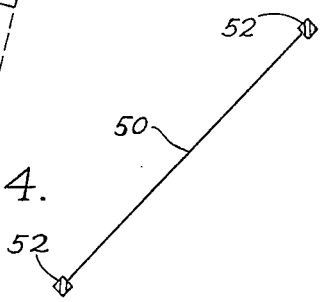
FIG. 4 is a detailed enlarged view of the beam splitter component of the apparatus of the invention in its pellicle embodiment.

Such a pellicle 50 is shown in FIG. 4. It is mounted in a frame 52.

Beam splitting pellicles are well known in the art. They comprise clear, cast plastic films of optical quality approximately 0.0003 inch thick cemented under tension to metal frames which have been lapped optically flat. Suitable films are made from cellulose acetate, polyester, or, particularly, polyethylene tetraphthalate.

As with the other classes of beam splitters, the base film may be coated with a neutral reflective coating which can be applied by vacuum evaporation. Suitable coatings comprise coatings of aluminum, zinc sulfide, antimony sulfide, magnesium fluoride, or a dielectric such as cryolite (sodium aluminum fluoride). These and other pellicles have the above described property of splitting or separating a beam of incident light into two component beams.

Figure 8:
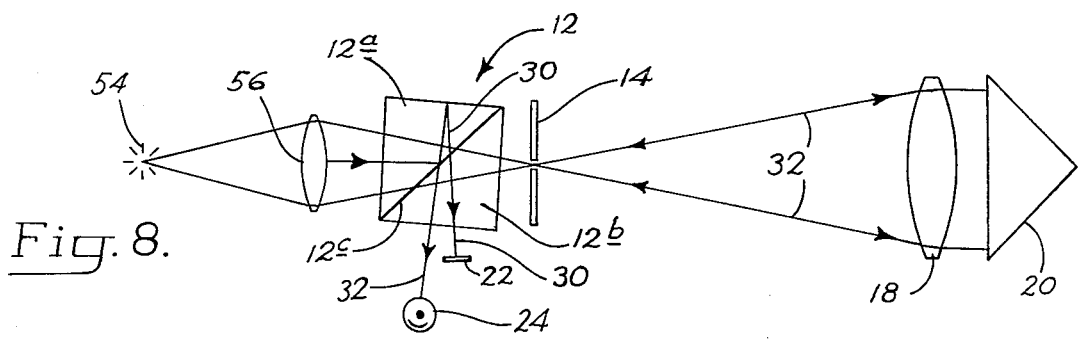
FIG. 8 is a schematic plan view similar to FIGS. 1 and 2, but illustrating the apparatus of the invention using an alternate light source, i.e. incandescent light.

The principle of separating the signal beam from the reference beam is not limited to the use of laser light. For instance, instead of a laser a more conventional light source such as incandescent light 54 may be used, FIG. 8. Since light from such a light source spreads out considerably more than light from a laser, a condenser lens 56 is placed between the light source and the pinhole.

Light leaving the pinhole in this case is already divergent and does not require a diverging lens 16 as before. The light proceeds to lens 6 and the prism to be tested 20. On return, the light is again split into two components, the signal beam 32 and the reference beam 30. These are measured, or blocked, as described above.

Experimental observation and a comparison of the two procedures i.e. the one using a laser light source and the other using an incandescent light source have shown that when a laser is used as a light source, the noise level is only about one-tenth that obtained with a more conventional light source. Therefore, the use of the prism testing photometer in conjunction with a laser is the preferred embodiment of my invention.

Turning now to a consideration of the question of the direction and amount of rotation of beam splitter 12 in order to obtain the desired result:

I have found that the crucial separation of signal beam and reference beam occurs on rotation in both the clockwise and the counterclockwise direction. When turning the cube clockwise, as shown in FIG. 2, the signal beam is put on the left; when turning the cube counterclockwise, the signal is put on the right. With reference to the amount of separation achieved by the practice of my method, and with reference to FIG. 3, it has been found that if the beam splitter cube is turned clockwise through an angle $\alpha$, this angle becomes the angle of incidence of the light on the left-hand face of the cube. Then from Snell's law, $$(\sin \alpha / \sin \beta) = (n_2/n_1) = (n/n_o) = n$$

where n is the refractive index of the material of the cube and $n_o$ is the refractive index of the medium outside the cube, generally air for which $n_o = 1$. It follows that $$\sin \beta = (\sin \alpha / n)$$

Furthermore, following the geometry of the light passing through and reflected inside the cube, $$\beta = \beta I = \beta II = \beta III = \beta IV$$

At the exit face,
$$\sin \alpha I = n \sin \beta IV = n \sin \beta$$

and therefore, $$\alpha = \alpha I$$

which means that the signal beam, beam 32 in FIG. 4, emerges from the side face of the cube subtending an angle with the surface normal which is equal in magnitude (but opposite in direction) to the angle of incidence of the light impinging on the front face.

From the construction in FIG. 4, it also follows that $$\tan \beta = \frac{d/2}{w} = \frac{d}{2w}$$

where w is the width of the cube and d the separation of the two beams as they are emerging from the cube. This separation, d, therefore is $$d = 2w \tan \beta = 2w \tan (\sin^{-1} \sin \alpha / n)$$

For instance, if the cube is made out of BK7 glass whose refractive index at a wavelength of 632.8 nanometers is 1.515, and if the cube is 30 millimeters wide and if it is turned through 2 degrees, then the separation of the two beams as they emerge from the cube is $$d = (2)(30) \tan (\sin^{-1} \sin 2°/1.515) = 2 \text{ mm}.$$

With reference to the degree of rotation, it has been found that the outside practical limit of rotation of beam splitter 12 is ±10°. A rotation of ±5° is preferred, with a rotation of about 2° being specifically preferred.

The influence of beam splitter rotation on prism test results is illustrated with reference to FIGS. 10 and 11.

Figure 10:
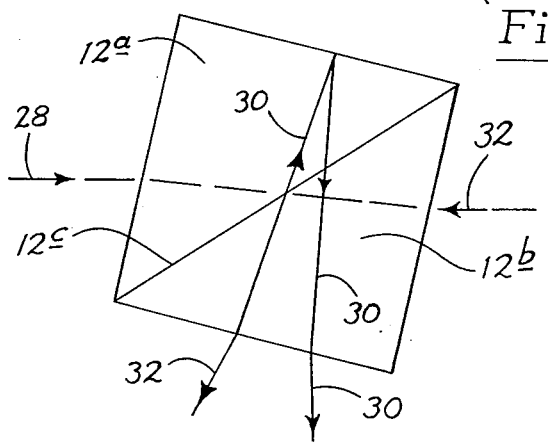
FIGS. 10 and 11 are schematic views illustrating the effect of beam splitter rotation on prism reflectance.
Figure 11:
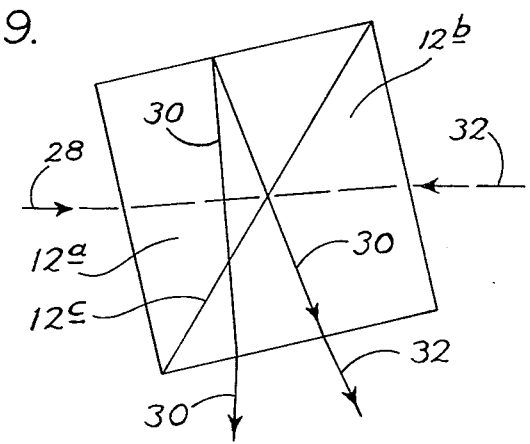

In FIG. 10 is illustrated clockwise rotation and in FIG. 11 counterclockwise rotation. In both cases, signal and reference beams have become clearly separate.

Consider the limiting case where boundary 12c is represented by a membrane suspended in air. Assume that the membrane has a refractive index of $n = 1.49$ which is a typical refractive index of many plastics such as polymethyl methacrylate. An index of 1.49 is an extreme case, with the highest possible difference between the two refractive indices, 1.49 for the membrane and 1.00 for air. The problem now becomes one of total internal reflection. Since the minimum angle of total internal reflection is given by $$\sin \gamma = (n_2/n_1)$$

we find that $$\gamma = \sin^{-1}(n_2/n_1) = \sin^{-1}(1/1.49) = 42.2°$$

which implies a rotation of the membrane counterclockwise through an angle of $$\alpha = 45° - 42.2° = 2.8°.$$

Furthermore, if the beamsplitter were again a cube, and the dividing boundary a clear, empty gap, then $$\alpha = \sin^{-1}(1/1.515) = 41.3°$$

which angle now refers to light still traveling inside the cube. This light emerges from the front face of the cube at an angle of $$\beta = 45° - \gamma = 45° - 41.3° = 3.7°$$

Using Snell's law of refraction, $(\sin \alpha / \sin \beta) = (n_2/n_1)$ we then find the angle of incidence on the front face, $$\alpha = \sin^{-1}[\sin (n_2/n_1)] = \sin^{-1}[\sin 3.7°(1.515/1.000)] = 5.6°$$

This angle is the same as the angle of rotation of the cube. This is the theoretical limit for the particular plastic having a refractive index of $n = 1.49$, at least as far as total internal reflection is concerned.

Experimental observation shows that the signal beam does not simply and abruptly disappear, but that it gradually fades out.

Again with reference to FIGS. 10 and 11 it has been found experimentally that when the cube is turned clockwise the signal beam 32 is located on the left and the reference beam 30 on the right. The signal beam fades out at a rotation of about 3.2° from the normal direction (with the light incident on the cube at right angles).

On rotation counterclockwise, FIG. 11, the signal beam 32 is on the right, the reference beam 30 on the left. In this case the signal beam fades out at about 7.3°. These angles constitute the limits of rotation in both the clockwise and counterclockwise direction.

On the other hand, if the cube is turned by too small an angle, separation of the two beams is too small, and blocking one of them becomes too difficult. At zero rotation or normal incidence, as mentioned earlier, signal and reference beams are not separated at all. The operative angle of rotation, as I have shown both experimentally and theoretically, lies within the broad limit of ±10° and the preferred limits of ±5°. At a rotation of 2° clockwise, a separation of the beams at the exit face of about 2 mm. is obtained. This is a desirable separation for the purposes of my invention.

OPERATION

The steps in the performance of the method of my invention are as follows:

First mount the light generating source such as laser 10 so that the optical axis is parallel to and at an appropriate height above, the optical bench rail.

Remove all elements and let the laser beam fall exactly in the center of the empty prism holder.

Insert beam splitter 12 and let the beam pass through its center. Turn the beam splitter by a small amount (a few degrees) in a clockwise direction as seen from the top. This gives two beams, the signal beam and the reference beam, properly separated.

Move pinhole 14 into the path. The distance from beam splitter 12 to the pinhole 14 is not critical but should be as short as possible. Hold a white card to the right of the cross motion assembly mounting the pinhole and align the pinhole up and down and sideways so that as much light as possible passes through and the spot of light is centered.

Place large lens 18 at a distance of approximately 60 cm. from minus lens 16 and adjust the lens to the correct height. Place (empty) prism holder to the right of lens 18. The distance from lens 18 to the prism holder is not critical but should be as short as possible. Hold a white sheet of paper to the right of the prism holder and readjust all four spindles on cross motion stages until the lighted field is as symmetrical, fully illuminated, and centered with respect to the prism holder as possible.

Place test prism 20 in the holder. Hold a white card between the beam splitter 12 and photodetector 24. Move lens 18 back and forth along the bench until the light returned by the prism that is the left hand dot as seen on the card, is brightest. Cautiously rotate the beam splitter about its vertical axis until the two dots are 2-4 mm. apart.

The apparatus now is ready for testing of the prisms with the magnitude of the readings on the ammeter associated with photodetector 24 giving an exact indication of the reflecting efficiency of the prism.

Experimental results when using this principle indicate that in the conventional mode, with the beam splitter cube oriented at right angles, i.e. the position of FIG. 1, typical test results averaged over at least 20 runs and adjusted for 100 for good prisms were

| |
|---|
| good prisms 100 |
| less than satisfactory prisms 79 |
| noise level 21 |

In contrast, with my signal-reference beam separation technique in which the beam splitter cube is slightly rotated, I obtained average results as follows:

| |
|---|
| good prisms 100 |
| less than satisfactory prisms 76 |
| noise level 2 |

This shows that the noise level could be reduced from 21 percent to 2 percent of the return light, a better than 10-fold improvement over conventional techniques for prism testing.

Having thus described my invention in preferred embodiments, I claim:

1. Apparatus for testing optical retrodirective prisms for light reflection efficiency, comprising:
   (a) light generating means for generating a beam of light, (b) optical beam splitter means in the path of the beam to generate a signal beam and a reference beam, positioned at a predetermined angle other than 45° with reference to the axis of said beam of light, (c) aligned pinhole means, lens means and a retrodirective prism positioned in the path of the separated signal beam for reflection by the prism of the signal beam back substantially parallel to its initial path, through the lens means, pinhole means and beam splitter, and (d) light intensity measuring means positioned in the path of the reflected signal beam for measuring the intensity thereof, and hence the efficiency of the prism.

2. The apparatus of claim 1 wherein the beam splitter is positioned at an angle of ±10° with reference to the beam axis.

3. The apparatus of claim 1 wherein the beam splitter is positioned at an angle of ±5° with reference to the beam axis.

4. The apparatus of claim 1 wherein the light generating means comprises laser light generating means.

5. The apparatus of claim 1 wherein the light generating means comprises laser light generating means, and wherein diverging lens means and converging lens means are inserted in downstream sequence between the pinhole means and the prism holding means.

6. The apparatus of claim 1 wherein the light generating means comprises incandescent light generating means.

7. The apparatus of claim 1 wherein the light generating means comprises incandescent light generating means, and wherein a condenser lens is located between the light generating means and the beam splitter means, and a converging lens is located between the pinhole means and the prism.

8. The apparatus of claim 1 wherein the beam splitter means comprises a glass cube type beam splitter.

9. The apparatus of claim 1 wherein the beam splitter means comprises a pellicle type beam splitter.

10. The apparatus of claim 1 including light stop means positioned for blocking the separated reference beam.

11. The apparatus of claim 1 including two light intensity measuring means, one positioned for intercepting the separated signal beam and the other positioned for intercepting the separated reference beam.

12. The apparatus of claim 1 wherein the light intensity measuring means is positioned in the path of both the reflected signal beam and the separated reference beam and including shutter means placed in front of the light intensity measuring means for selectively impinging one or the other of the beams thereon.

13. The method of testing optical retrodirective prisms for light reflection efficiency, comprising:

(a) generating a beam of light, (b) passing the beam through an optical beam splitter to generate a signal beam and a reference beam, (c) positioning the beam splitter at a predetermined angle to the axis of the beams, other than 45°, (d) passing the signal beam through pinhole means and into the prism to be tested, (e) reflecting the signal beam out of the prism substantially parallel to its initial path, back through the pinhole means and beam splitter, and (f) measuring the intensity of the reflected signal beam.

14. The method of claim 13 wherein the beam of light is a laser beam.

15. The method of claim 13 including the step of positioning the beam splitter at an angle of plus or minus 10° with reference to the axis of the beams.

16. The method of claim 13 including the step of positioning the beam splitter at an angle of plus or minus 5° with reference to the axis of the beams.

17. The method of claim 13 including the step of stopping the separated reference beam.

18. The method of claim 13 including the step of measuring the intensity of the separated reference beam and comparing its intensity with the intensity of the separated signal beam for evaluation of prism efficiency.

* * * * *